(12) United States Patent
Takahashi et al.

(10) Patent No.: US 12,193,641 B2
(45) Date of Patent: Jan. 14, 2025

(54) ENDOSCOPE SYSTEM

(71) Applicant: FUJIFILM Corporation, Tokyo (JP)

(72) Inventors: Nobuharu Takahashi, Kanagawa (JP);
Motohiko Matsushita, Kanagawa (JP);
Takuro Ide, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/988,774

(22) Filed: Nov. 17, 2022

(65) Prior Publication Data

US 2023/0074673 A1 Mar. 9, 2023

Related U.S. Application Data

(63) Continuation of application No. 16/780,910, filed on Feb. 4, 2020, now Pat. No. 11,553,832, which is a (Continued)

(30) Foreign Application Priority Data

Jun. 5, 2015 (JP) .................................. 2015-114497

(51) Int. Cl.
*A61B 1/00* (2006.01)
*A61B 1/005* (2006.01)
(Continued)

(52) U.S. Cl.
CPC ...... *A61B 1/00154* (2013.01); *A61B 1/00071* (2013.01); *A61B 1/00078* (2013.01);
(Continued)

(58) Field of Classification Search
CPC ............ A61B 1/00071; A61B 1/00078; A61B 1/00082; A61B 1/0008; A61B 1/00131; A61B 1/00133; A61B 1/00135; A61B 1/00142; A61B 1/00151; A61B 1/00154; A61B 1/00156; A61B 1/005; A61B 1/0125; A61B 1/0016; A61B 1/008; A61B 1/01; A61B 1/273; A61B 1/2733; A61B 1/2736; A61B 1/31; A61M 25/0102
See application file for complete search history.

(56) References Cited

U.S. PATENT DOCUMENTS 5,885,208 A * 3/1999 Moriyama ........... A61B 1/0051
600/146
5,941,815 A * 8/1999 Chang ................. A61B 1/00151
600/114
(Continued)

*Primary Examiner* — Ryan N Henderson
(74) *Attorney, Agent, or Firm* — JCIPRNET

(57) ABSTRACT

An endoscope system includes an endoscope, and an insertion auxiliary tool into which the endoscope is inserted. A flexible portion of the insertion section of the endoscope includes, from a distal end side toward a proximal end side, a low flexural rigidity portion, and a flexural rigidity varying portion in which a flexural rigidity increases from the distal end side toward the proximal end side. When at least a part of the flexible portion projects from a distal end opening of the tube body, a position of the proximal end of the low flexural rigidity portion is positioned closer to a proximal end of the insertion auxiliary tool than the distal end opening of the tube body from the proximal end of the insertion auxiliary tool.

17 Claims, 11 Drawing Sheets

Related U.S. Application Data continuation-in-part of application No. 15/170,930, filed on Jun. 1, 2016, now abandoned.

(51) Int. Cl.
  *A61B 1/31* (2006.01)
  *A61M 25/01* (2006.01)

(52) U.S. Cl.
  CPC ............... *A61B 1/005* (2013.01); *A61B 1/31* (2013.01); *A61M 25/0102* (2013.01); *A61B 1/00082* (2013.01)

(56) References Cited

U.S. PATENT DOCUMENTS

| | | | | |
|---|---|---|---|---|
| 6,572,538 B2* | 6/2003 | Takase | A61B 1/005 | 600/144 |
| 6,860,849 B2* | 3/2005 | Matsushita | A61L 29/085 | 600/140 |
| 7,041,052 B2* | 5/2006 | Saadat | A61B 1/0052 | 600/114 |
| 7,481,793 B2* | 1/2009 | Abrams | A61M 25/0662 | 604/99.01 |
| 7,537,562 B2* | 5/2009 | Takano | A61B 1/00082 | 600/114 |
| 7,713,191 B2* | 5/2010 | Sekiguchi | A61B 1/31 | 600/116 |
| 7,833,150 B2* | 11/2010 | Yamamoto | A61B 1/00082 | 600/116 |
| 7,909,755 B2* | 3/2011 | Itoi | A61B 1/00154 | 600/114 |
| 7,955,253 B2* | 6/2011 | Ewers | A61B 1/00082 | 600/114 |
| 8,012,084 B2* | 9/2011 | Machida | A61B 1/00091 | 600/116 |
| 8,083,670 B2* | 12/2011 | Ikeda | A61B 1/018 | 600/116 |
| 8,088,063 B2* | 1/2012 | Fujikura | A61B 17/3415 | 604/167.03 |
| 8,092,372 B2* | 1/2012 | Machida | A61B 1/31 | 600/116 |
| 8,128,614 B2* | 3/2012 | Abrams | A61M 25/0662 | 604/536 |
| 8,221,308 B2* | 7/2012 | Noguchi | A61M 25/01 | 600/117 |
| 8,366,606 B2* | 2/2013 | Watanabe | A61B 1/00078 | 600/114 |
| 8,439,825 B2* | 5/2013 | Sekiguchi | A61B 1/31 | 600/116 |
| 8,579,802 B2* | 11/2013 | Robertson | A61B 1/0051 | 600/114 |
| 9,629,535 B2* | 4/2017 | Lal | A61B 1/31 | |
| 2002/0002323 A1* | 1/2002 | Moriyama | A61B 1/0051 | 600/130 |
| 2002/0010386 A1* | 1/2002 | Matsushita | A61L 29/12 | 600/140 |
| 2002/0013512 A1* | 1/2002 | Sendai | A61B 5/0084 | 600/118 |
| 2002/0161281 A1* | 10/2002 | Jaffe | A61B 1/00154 | 600/114 |
| 2003/0233025 A1* | 12/2003 | Saadat | A61B 1/00082 | 600/114 |
| 2004/0080613 A1* | 4/2004 | Moriyama | A61B 1/31 | 348/E7.086 |
| 2004/0176683 A1* | 9/2004 | Whitin | A61B 5/068 | 600/117 |
| 2004/0186349 A1* | 9/2004 | Ewers | A61B 1/31 | 600/114 |
| 2004/0186350 A1* | 9/2004 | Brenneman | A61M 25/09 | 600/146 |
| 2005/0059861 A1* | 3/2005 | Nishiie | A61B 1/0055 | 600/140 |
| 2005/0124856 A1* | 6/2005 | Fujikura | A61B 17/3417 | 600/156 |
| 2005/0131343 A1* | 6/2005 | Abrams | A61M 25/0662 | 606/41 |
| 2005/0137454 A1* | 6/2005 | Saadat | A61B 1/00135 | 600/129 |
| 2005/0137455 A1* | 6/2005 | Ewers | A61B 1/0052 | 600/114 |
| 2005/0137456 A1* | 6/2005 | Saadat | A61B 1/0055 | 600/114 |
| 2005/0137457 A1* | 6/2005 | Machida | A61B 1/00082 | 600/116 |
| 2005/0159644 A1* | 7/2005 | Takano | A61B 1/00082 | 600/116 |
| 2005/0165273 A1* | 7/2005 | Takano | A61B 1/01 | 600/116 |
| 2005/0171400 A1* | 8/2005 | Itoi | A61B 1/00082 | 600/116 |
| 2005/0215855 A1* | 9/2005 | Machida | A61B 1/00082 | 600/156 |
| 2005/0215856 A1* | 9/2005 | Fujikura | A61B 1/00082 | 600/116 |
| 2005/0222496 A1* | 10/2005 | Sekiguchi | A61B 1/0016 | 600/116 |
| 2005/0222500 A1* | 10/2005 | Itoi | A61B 1/00082 | 600/116 |
| 2006/0025652 A1* | 2/2006 | Vargas | A61B 1/0055 | 600/114 |
| 2006/0100480 A1* | 5/2006 | Ewers | A61B 1/00082 | 600/114 |
| 2006/0111610 A1* | 5/2006 | Machida | A61B 1/00091 | 600/116 |
| 2006/0116549 A1* | 6/2006 | Sekiguchi | A61B 1/00055 | 600/116 |
| 2006/0135847 A1* | 6/2006 | Koch | A61B 1/0011 | 600/104 |
| 2006/0135848 A1* | 6/2006 | Koch | A61B 1/0058 | 600/104 |
| 2006/0271095 A1* | 11/2006 | Rauker | A61B 1/31 | 606/197 |
| 2006/0287666 A1* | 12/2006 | Saadat | A61M 25/1011 | 606/198 |
| 2007/0010785 A1* | 1/2007 | Sekiguchi | A61B 1/00082 | 604/920 |
| 2007/0015965 A1* | 1/2007 | Cox | A61B 1/00078 | 600/116 |
| 2007/0043261 A1* | 2/2007 | Watanabe | A61B 1/00071 | 600/152 |
| 2007/0249901 A1* | 10/2007 | Ohline | A61B 5/065 | 600/117 |
| 2007/0270645 A1* | 11/2007 | Ikeda | A61B 1/12 | 600/116 |
| 2007/0299308 A1* | 12/2007 | Fujikura | A61M 25/0662 | 600/115 |
| 2008/0033246 A1* | 2/2008 | Matsui | A61B 1/00082 | 600/115 |
| 2008/0146875 A1* | 6/2008 | Noguchi | G02B 23/2484 | 600/117 |
| 2008/0228034 A1* | 9/2008 | Fujikura | A61B 1/00082 | 600/114 |
| 2008/0249356 A1* | 10/2008 | Motai | A61B 1/00082 | 600/114 |
| 2009/0062608 A1* | 3/2009 | Miyoshi | A61B 1/00082 | 600/114 |
| 2009/0118582 A1* | 5/2009 | Tsumaru | A61B 1/00094 | 600/114 |
| 2009/0124857 A1* | 5/2009 | Viola | A61B 1/0055 | 600/141 |
| 2009/0124978 A1* | 5/2009 | Abrams | A61M 25/0662 | 604/164.01 |
| 2009/0156896 A1* | 6/2009 | Kura | A61B 1/00078 | 600/118 |
| 2009/0287051 A1* | 11/2009 | Itoi | A61B 1/0655 | 604/114 |
| 2010/0022832 A1* | 1/2010 | Makiyama | A61B 1/015 | 600/115 |

(56) References Cited

U.S. PATENT DOCUMENTS

| | | | |
|---|---|---|---|
| 2010/0286479 A1* | 11/2010 | Ashida | A61M 25/10184 |
| | | | 600/116 |
| 2010/0292537 A1* | 11/2010 | Ashida | A61B 1/018 |
| | | | 600/116 |
| 2011/0004063 A1* | 1/2011 | Nakamura | A61B 1/00135 |
| | | | 600/115 |
| 2011/0137120 A1* | 6/2011 | Itoi | A61B 1/00082 |
| | | | 600/114 |
| 2011/0137121 A1* | 6/2011 | Itoi | A61B 1/01 |
| | | | 600/114 |
| 2012/0071722 A1* | 3/2012 | Nakamura | A61B 1/0051 |
| | | | 600/140 |
| 2012/0220829 A1* | 8/2012 | Fujikura | A61B 1/00154 |
| | | | 600/114 |
| 2012/0232347 A1* | 9/2012 | Fujikura | A61B 17/3417 |
| | | | 600/114 |
| 2013/0023920 A1* | 1/2013 | Terliuc | A61B 1/31 |
| | | | 606/192 |
| 2014/0018625 A1* | 1/2014 | Lal | A61B 1/31 |
| | | | 600/115 |
| 2014/0094649 A1* | 4/2014 | Ito | A61B 1/0669 |
| | | | 600/114 |
| 2021/0095753 A1* | 4/2021 | Uchida | G02B 23/2476 |

* cited by examiner

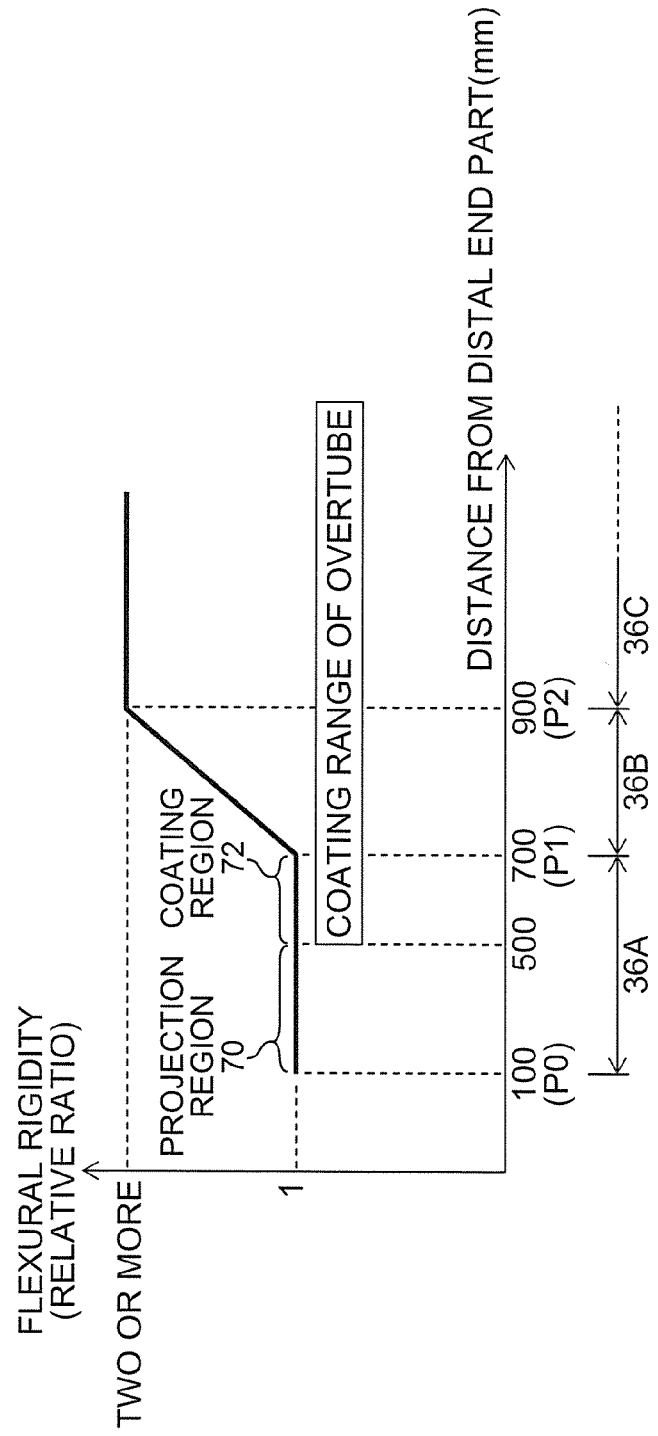

ENDOSCOPE SYSTEM

CROSS-REFERENCE TO RELATED APPLICATIONS

This application is a continuation application of and claims the priority benefit of U.S. application Ser. No. 16/780,910, filed on Feb. 4, 2020. The prior U.S. application Ser. No. 16/780,910 is a continuation-in-part application of and claims the priority benefit of U.S. application Ser. No. 15/170,930, filed on Jun. 1, 2016, which claims priority under 35 U.S.C. § 119 to Japanese Patent Application No. 2015-114497, filed on Jun. 5, 2015. The entirety of each of the above-mentioned patent applications is hereby incorporated by reference herein and made a part of this specification.

BACKGROUND OF THE INVENTION

Field of the Invention

The present invention relates to an endoscope system in which an endoscope and an insertion auxiliary tool are used in combination with each other, and more particularly to flexural rigidity of an insertion section of the endoscope.

Description of the Related Art

An endoscope is sometimes used for diagnosis and an operation on the stomach, duodenum, small intestine, and the like. To improve insertion of an endoscope at the time of diagnosis or an operation, it is known to vary hardness of an insertion section of the endoscope in response to operation by an operator (refer to Japanese Patent Application Laid-Open No. 2013-027466 (Patent Literature 1), and Japanese Patent Application Laid-Open No. 2003-260021 (Patent Literature 2), for example).

Unfortunately, when a conventional endoscope, such as the one disclosed in Patent Literature 1 or 2, is used alone in diagnosis and an operation, the insertion section may not become a linear state due to adhesion by the operation, fixation of the intestinal tract by the ligament of Treitz, or the like. As a result, the insertion section is deformed inside the stomach or the like to cause so-called "difficult insertion case", in which insertion force cannot be transmitted to a distal end part and the distal end part cannot be inserted forward, in many cases. Thus, there is provided an endoscope system in which an endoscope with a balloon, and an overtube (insertion auxiliary tool) with a balloon, are used in combination with each other (refer to Japanese Patent Application Laid-Open No. 2013-090875 (Patent Literature 3), for example). Also in this kind of endoscope system, there is known art that varies hardness of an insertion section of an endoscope (refer to Japanese Patent Application Laid-Open No. 2005-334474 (Patent Literature 4), for example).

SUMMARY OF THE INVENTION

However, although the art disclosed in Patent Literature 4 above enables to vary hardness of an insertion section of an endoscope, a hardness value is constant within a range in which a hardness variable mechanism is provided (such as a range of L in FIG. 1 of Patent Literature 4). In contrast, in a postoperative patient to whom the Roux-en-Y Method, or the like, is applied, a level of flexural rigidity required for an insertion section, and a position or a range requiring the flexural rigidity, are different depending on conditions, such as a removal range of the stomach (entire removal or partial removal), and an observation position. Thus, in the conventional art such as disclosed in Patent Literatures 1 to 4, it has been difficult to meet requirements of this kind of flexural rigidity, and accordingly a problem arises that a load on a patient increases.

The present invention is made in light of the above-mentioned circumstances, and the present invention aims to provide an endoscope system capable of securing appropriate flexural rigidity of an insertion section.

To achieve the object describe above, an endoscope system in accordance with a first aspect of the present invention includes: an endoscope including: an insertion section to be inserted into a body; and an operation section connected to a proximal end side of the insertion section, the insertion section having a distal end hard portion, a bending portion connected to a proximal end side of the distal end hard portion and a flexible portion connected to a proximal end side of the bending portion; and an insertion auxiliary tool including a tube body having a distal end opening, a proximal end opening and an insertion passage into which the insertion section is inserted from the proximal end opening, the insertion section being movable back and forth along a center axis direction of the tube body, the tube body being configured to have a length that allows at least a part of the flexible portion to project from the distal end opening when the insertion section is positioned at a distal end position within a back-and-forth movable range in which the insertion section is movable with respect to the tube body, wherein the flexible portion includes: a low flexural rigidity portion that is positioned on a distal end side of the flexible portion; a high flexural rigidity portion that is positioned on a proximal end side of the flexible portion, the high flexural rigidity portion having increased flexural rigidity relative to the low flexural rigidity portion; and a flexural rigidity varying portion that is positioned between the low flexural rigidity portion and the high flexural rigidity portion, the flexural rigidity varying portion having a flexural rigidity which increases from a low flexural rigidity portion side toward a high flexural rigidity portion side, wherein the flexural rigidity varying portion has an average rate of change of flexural rigidity in a longitudinal axial direction of the insertion section, the average rate of change of flexural rigidity being larger than an average rate of change of flexural rigidity in the low flexural rigidity portion in the longitudinal axial direction of the insertion section, and larger than an average rate of change of flexural rigidity in the high flexural rigidity portion in the longitudinal axial direction of the insertion section, wherein the flexural rigidity in the low flexural rigidity portion varies in the longitudinal axial direction of the insertion section, and when the insertion section is positioned at a distal end position within the back-and forth movable range with respect to the tube body, a position of the proximal end of the low flexural rigidity portion is positioned closer to a proximal end of the insertion auxiliary tool than the distal end opening of the tube body from the proximal end of the insertion auxiliary tool, in the longitudinal axial direction of the insertion section.

According to the first aspect of the present invention, when the insertion section is positioned at the distal end position within the back-and-forth movable range in which the insertion section is movable with respect to the tube body, the proximal end position of the low flexural rigidity portion is positioned on the proximal end side with respect to the distal end opening of the tube body, in the longitudinal axial direction of the insertion section. As a result, a part of the insertion section which is exposed from the tube body and a part on the distal end side of a region where the insertion section is covered with the tube body form the low flexural rigidity portion that is a portion having a minimum flexural rigidity. Thus, the rigidity of the distal end part of the flexible portion is not too high and the insertion into a site with a large bend or curvature can be performed easily. Accordingly, when such the site is observed, a load on a patient can be reduced.

In this way, the endoscope system in accordance with the first aspect can secure an appropriate flexural rigidity of the insertion section.

In the first aspect, a range in which each of the low flexural rigidity portion, the high flexural rigidity portion and the flexural rigidity varying portion, is provided, and a value of flexural rigidity in each of the portions, may be set depending on conditions such as estimated patient's condition (such as state of evisceration), and a position to be observed. The flexural rigidity in the flexural rigidity varying portion may be set so as to uniformly increase from the low flexural rigidity portion side toward the high flexural rigidity portion side (a rate of increase in flexural rigidity is constant), or the rate of increase in flexural rigidity may be set so as to vary in the middle between the low flexural rigidity portion and the high flexural rigidity portion. Moreover, in the first aspect and each aspect below, the "average rate of change of flexural rigidity" in each of the low flexural rigidity portion, the flexural rigidity varying portion, and the high flexural rigidity portion, is a value expressed by $(Y-X)/Z$, where X is a value of the flexural rigidity in each of the portions at a distal end position and Y is a value in each of the portions at a proximal end position, and Z is a length of each of the portions (along a longitudinal direction of the insertion section) (here, X, Y, and Z are more than zero, and Y is more than X).

To achieve the object describe above, an endoscope system in accordance with a second aspect of the present invention includes: an endoscope including: an insertion section to be inserted into a body; and an operation section connected to a proximal end side of the insertion section, the insertion section having a distal end hard portion, a bending portion connected to a proximal end side of the distal end hard portion and a flexible portion connected to a proximal end side of the bending portion; and an insertion auxiliary tool including a tube body having a distal end opening, a proximal end opening and an insertion passage into which the insertion section is inserted from the proximal end opening, the insertion section being movable back and forth along a center axis direction of the insertion passage, the tube body including a contact part which abuts on the endoscope on a proximal end side of the tube body, the tube body being configured to have a length that allows at least a part of the flexible portion to project from the distal end opening when the endoscope abuts on the contact part, wherein the flexible portion includes: a low flexural rigidity portion that is positioned on a distal end side of the flexible portion; a high flexural rigidity portion that is positioned on a proximal end side of the flexible portion, the high flexural rigidity portion having increased flexural rigidity relative to the low flexural rigidity portion; and a flexural rigidity varying portion that is positioned between the low flexural rigidity portion and the high flexural rigidity portion, the flexural rigidity varying portion having a flexural rigidity which increases from a low flexural rigidity portion side toward a high flexural rigidity portion side, wherein the flexural rigidity varying portion has an average rate of change of flexural rigidity in a longitudinal axial direction of the insertion section, the average rate of change of flexural rigidity being larger than an average rate of change of flexural rigidity in the low flexural rigidity portion in the longitudinal axial direction of the insertion section, and larger than an average rate of change of flexural rigidity in the high flexural rigidity portion in the longitudinal axial direction of the insertion section, wherein the flexural rigidity in the low flexural rigidity portion varies in the longitudinal axial direction of the insertion section, and when the endoscope abuts on the contact part, a position of the proximal end of the low flexural rigidity portion is positioned closer to a proximal end of the insertion auxiliary tool than the distal end opening of the tube body from the proximal end of the insertion auxiliary tool, in the longitudinal axial direction of the insertion section.

According to the second aspect of the present invention, when the endoscope abuts on the contact part, the proximal end position of the low flexural rigidity portion is positioned on the proximal end side with respect to the distal end opening of the tube body, in the longitudinal axial direction of the insertion section. As a result, a part of the insertion section which is exposed from the tube body and a part on the distal end side of a region where the insertion section is covered with the tube body form the low flexural rigidity portion that is a portion having a minimum flexural rigidity. Thus, rigidity of a distal end part of the flexible portion is not too high and the insertion into a site with a large bend or curvature can be performed easily. Accordingly, when such the site is observed, a load on a patient can be reduced.

In this way, the endoscope system in accordance with the second aspect of the present invention can secure an appropriate flexural rigidity of the insertion section, as with the first aspect. In the second aspect also, the flexural rigidity in the flexural rigidity varying portion may be set so as to uniformly increase from the low flexural rigidity portion side toward the high flexural rigidity portion side (a rate of increase in flexural rigidity is constant), or the rate of increase in flexural rigidity may be set so as to vary in the middle between the low flexural rigidity portion and the high flexural rigidity portion.

According to a third aspect, in an endoscope system in accordance with any one of the first to second aspects, when a flexural rigidity at a distal end position of the flexural rigidity varying portion is indicated as a first flexural rigidity and a flexural rigidity at a proximal end position of the flexural rigidity varying portion is indicated as a second flexural rigidity, the second flexural rigidity is more than twice the first flexural rigidity.

According to a fourth aspect, in an endoscope system in accordance with any one of the first to third aspects, when a flexural rigidity at the distal end position of the flexural rigidity varying portion is indicated as the first flexural rigidity, a flexural rigidity at the proximal end position of the flexural rigidity varying portion is indicated as the second flexural rigidity and a flexural rigidity at a position having a maximum flexural rigidity in the tube body is indicated as third flexural rigidity, a difference between the first flexural rigidity and the second flexural rigidity is more than a half of the third flexural rigidity. The fourth aspect sets the difference between the first flexural rigidity and the second flexural rigidity to be more than half of the third flexural rigidity, thereby increasing the effect achieved by providing the flexural rigidity varying portion.

As described above, the endoscope system according to the present invention can secure an appropriate flexural rigidity of the insertion section.

BRIEF DESCRIPTION OF THE DRAWINGS

FIG. 6 is a graph showing an example of flexural rigidity of the flexible portion 36;

DETAILED DESCRIPTION OF THE EMBODIMENTS

Figure 1:
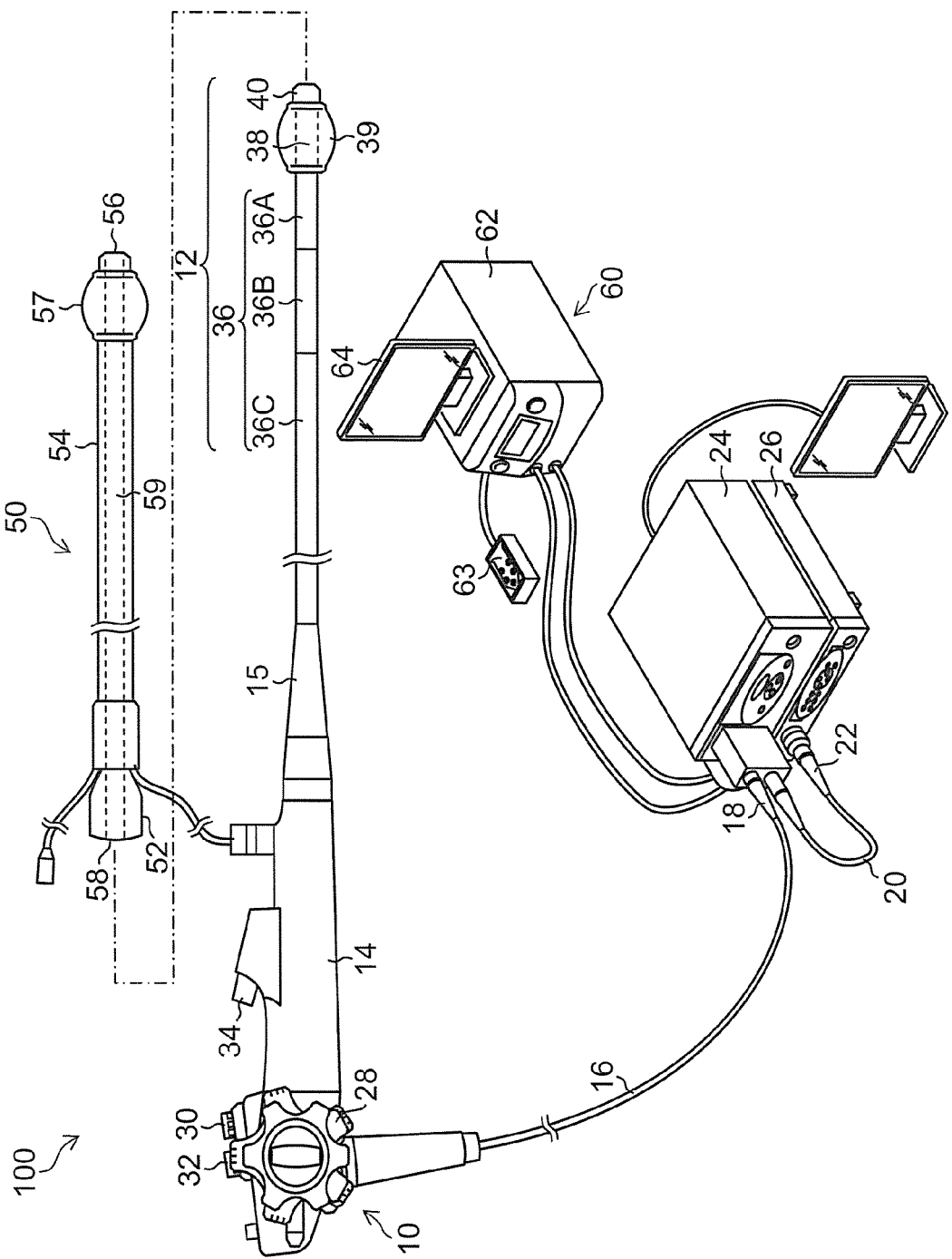
FIG. 1 shows a configuration of an endoscope system in accordance with one embodiment of the present invention.

An endoscope system in accordance with the present invention will be described below with reference to accompanying drawings. FIG. 1 shows a general configuration of an endoscope system 100 in accordance with the present embodiment.

(General Configuration of Endoscope System)

As shown in FIG. 1, the endoscope system 100 includes an endoscope 10 and the overtube 50. The endoscope 10 includes an insertion section 12 to be inserted into a body of a subject, and an operation section 14 is connected to a proximal end part of the insertion section 12. To the operation section 14, a universal code 16 is connected, and a connector 18 for a light source is provided at a distal end of the universal code 16. In addition, a cable 20 branches off from the connector 18 for a light source, and a connector 22 for a processor is connected to a distal end of the cable 20. The connector 18 for a light source and the connector 22 for a processor are detachably connected to a light source device 24 and a processor device 26, respectively. The overtube 50 is one embodiment of an insertion auxiliary tool.

(Configuration of Overtube)

The overtube 50 includes a holding section 52 to be held by an operator, and a tube body 54. The holding section 52 is a cylindrical body formed of hard material, such as resin. The tube body 54 is formed of flexible material, such as polyurethane, and has a cylindrical shape provided with a distal end opening 56 and a proximal end opening 58. The inside of the cylindrical part is configured to be an insertion passage 59 into which the insertion section 12 is inserted, and the insertion section 12 is movable back and forth in a center axis direction (X direction in FIG. 3) of the overtube 50. As described later, when the insertion section 12 is positioned at a distal end position within a back-and forth movable range in which the insertion section 12 is movable with respect to the overtube 50, an inner edge of the proximal end opening 58 abuts on a boot 15 of the insertion section 12. In the present aspect, the inner edge of the proximal end opening 58 constitutes a contact part.

In addition, a balloon 57 is attached to an outer peripheral surface of a distal end part of the tube body 54. The balloon 57 is formed of elastic material, such as rubber, and has a cylindrical shape. The balloon 57 is provided at its center with a bulging part. The balloon 57 is attached and fixed to the outer peripheral surface of the distal end part of the tube body 54 and is configured to be expanded or shrunk by fluid (such as air or water) that is supplied and sucked through a fluid conduit line (not shown). This kind of expansion and shrinkage of the balloon 57 is controlled by a balloon control device 60. The balloon control device 60 supplies and sucks fluid, or controls a pressure of the fluid to expand or shrink the balloon 57, or to maintain a state of the balloon 57. The balloon control device 60 includes: a device body 62 provided with a pump, a sequencer, and the like, a hand switch 63; and a balloon monitor 64.

(General Configuration of Insertion Section)

The insertion section 12 includes a flexible portion 36, a bending portion 38, and a distal end hard portion 40, which are sequentially connected in this order from a proximal end side (operation section 14 side) to a distal end side. The boot 15 of the insertion section 12 is provided at a portion of the flexible portion 36, closest to the proximal end. The boot 15 is formed (tapered) so as to gradually decrease in diameter from the proximal end side toward the distal end side.

(Configuration of Operation Section)

The operation section 14 includes: an angle knob 28 for bending operation; an air/water supply button 30 for injecting air, water, or the like, from the distal end of the insertion section 12 (an opening provided at the distal end hard portion 40 to be described later); a suction button 32; and the like. The operation section 14 is provided on its insertion section 12 side with a forceps entry port 34 from which various treatment tools are to be inserted.

In response to operation of the air/water supply button 30, air or water is supplied by an air/water supply device which is built in the light source device 24, and injected toward an observation window from an air/water supply nozzle. A forceps exit port is connected to a forceps channel (not shown) provided inside the insertion section 12 to communicate with the forceps entry port 34. A distal end of a treatment tool inserted from the forceps entry port 34 is exposed from the forceps exit port.

(Configuration of Flexible Portion)

Figure 2:
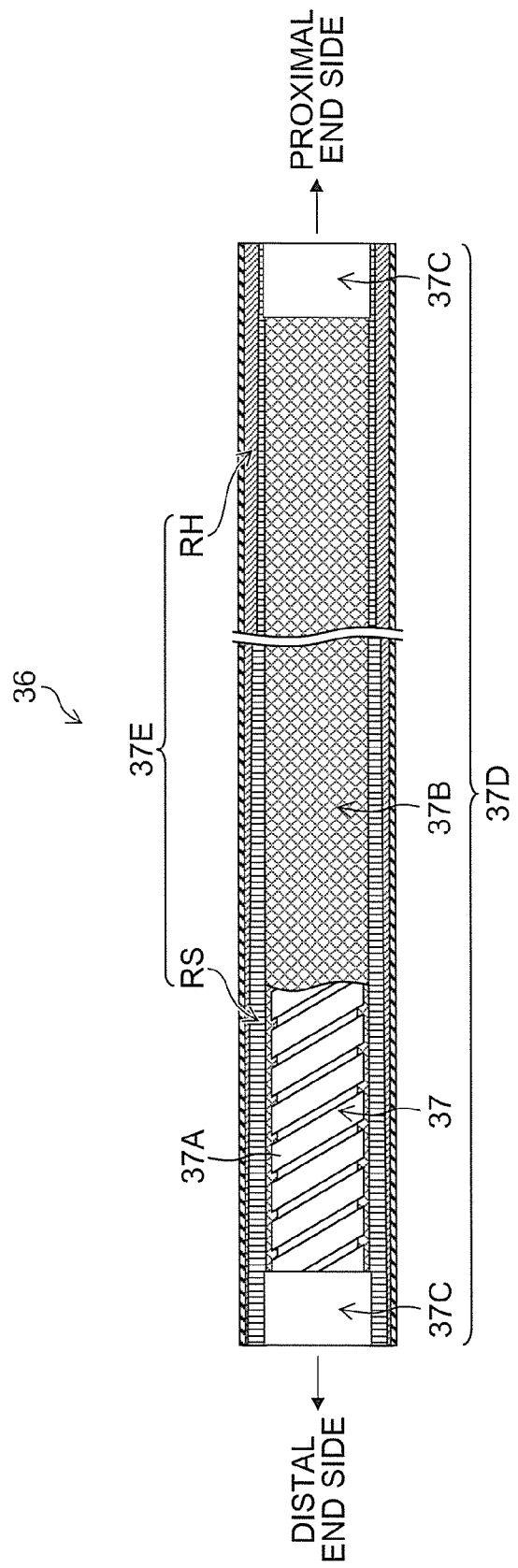
FIG. 2 is a sectional view showing a structure of a flexible portion 36 (near a flexural rigidity varying portion 36B)

As shown in FIG. 2, the flexible portion 36 has a laminated structure as follows: an innermost of the flexible portion 36 is a spiral tube 37 which is formed by spirally winding an elastic thin strip-like plate 37A; the outside of the spiral tube 37 is coated with a net 37B which is woven from metal wires, and then caps 37C are fitted into respective opposite ends of the spiral tube 37 to form a tubular body 37D; an outer skin 37E which is made of resin is laminated on an outer peripheral surface of the tubular body 37D.

(Flexural Rigidity of Flexible Portion)

The flexible portion 36 configured as above includes a low flexural rigidity portion 36A, a flexural rigidity varying portion 36B, and a high flexural rigidity portion 36C, in this order from the distal end side toward the proximal end side (refer to FIG. 1). A flexural rigidity of the low flexural rigidity portion 36A and the high flexural rigidity portion 36C is uniform along a longitudinal axial direction of the insertion section 12 (X direction in FIG. 3), and the high flexural rigidity portion 36C has a flexural rigidity that is relatively higher than a flexural rigidity of the low flexural rigidity portion 36A. The low flexural rigidity portion 36A and the high flexural rigidity portion 36C constitute a first flexural rigidity uniform portion and a second flexural rigidity uniform portion, in the present invention, respectively. On the other hand, a flexural rigidity of the flexural rigidity varying portion 36B uniformly increases from a low flexural rigidity portion 36A side (distal end side) to a high flexural rigidity portion 36C side (proximal end side) (details will be described later).

Figure 4A:
FIGS. 4A to 4C show examples of varying flexural rigidity with a material composition of an outer skin 37E of the flexible portion 36.

As shown in FIG. 2, the variations of flexural rigidity in the flexural rigidity varying portion 36B can be achieved by forming the outer skin 37E of the flexible portion 36 by resin layers RH and RS with different hardness, and varying thicknesses of the resin layers from the distal end side toward the proximal end side. Specifically, as shown in FIG. 4A, an outside part of the outer skin 37E is composed of a hard (high flexural rigidity) resin layer RH, and an inside part of the outer skin 37E is composed of a soft resin layer RS (having a flexural rigidity less than that of the resin layer RH). Then, within a range of the flexural rigidity varying portion 36B, the resin layer RS is increased in thickness at a first position P1 on the distal end side (low flexural rigidity portion 36A side). The resin layer RS is gradually reduced in thickness from the first position P1 toward a second position P2 on the proximal end side (high flexural rigidity portion 36C side) and increase a thickness of the resin layer RH, where the total thickness of the resin layers RH and RS is uniform. Accordingly, as shown in FIG. 4C, the flexural rigidity in the flexural rigidity varying portion 36B can uniformly increase from the distal end side toward the proximal end side (a rate of increase in flexural rigidity is constant).

Figure 4B:
Figure 4C:
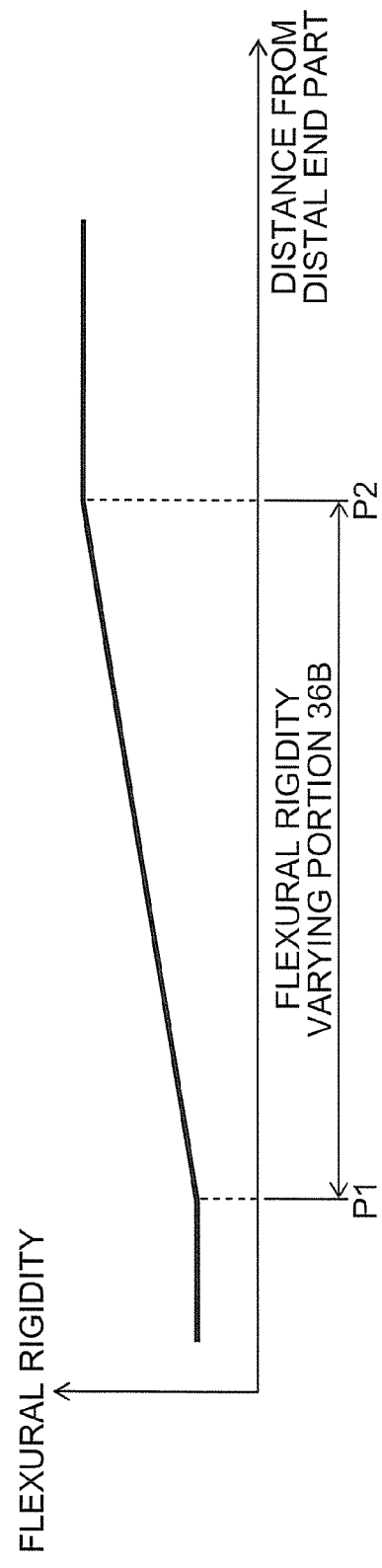

As shown in FIG. 4C, the variations of flexural rigidity also can be achieved by varying a mixing ratio of hard resin and soft resin, instead of varying the thickness of the resin layers. Specifically, as shown in FIG. 4B, a ratio of soft (low flexural rigidity) resin may be set high on the distal end side, and a ratio of hard (high flexural rigidity) resin may be increased from the distal end side toward the proximal end side. In addition, instead of using a plurality of resins, a thickness of a resin layer may be increased from the distal end side toward the proximal end side by using a single resin (thickness of the outer skin 37E is increased) to increase the flexural rigidity.

While the present embodiment describes the case where the flexural rigidity in the flexural rigidity varying portion 36B uniformly increases from the low flexural rigidity portion 36A side toward the high flexural rigidity portion 36C side (a rate of increase in flexural rigidity is constant), the present invention does not limit the variation of flexural rigidity to this kind of aspect. A rate of increase in flexural rigidity may vary from the low flexural rigidity portion 36A side toward the high flexural rigidity portion 36C side.

(Method of Measuring Flexural Rigidity)

Figure 5A:
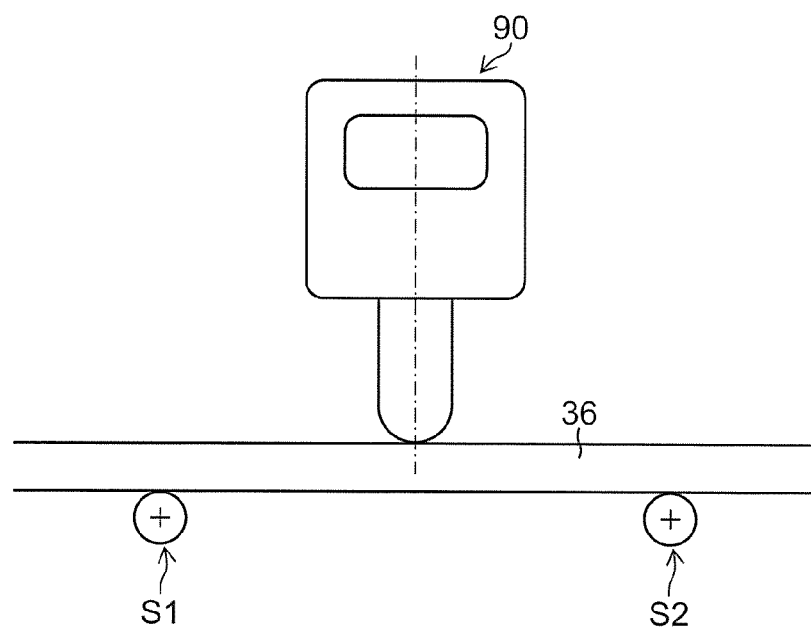
FIGS. 5A and 5B show states when the flexural rigidity of the flexible portion 36 is measured.
Figure 5B:
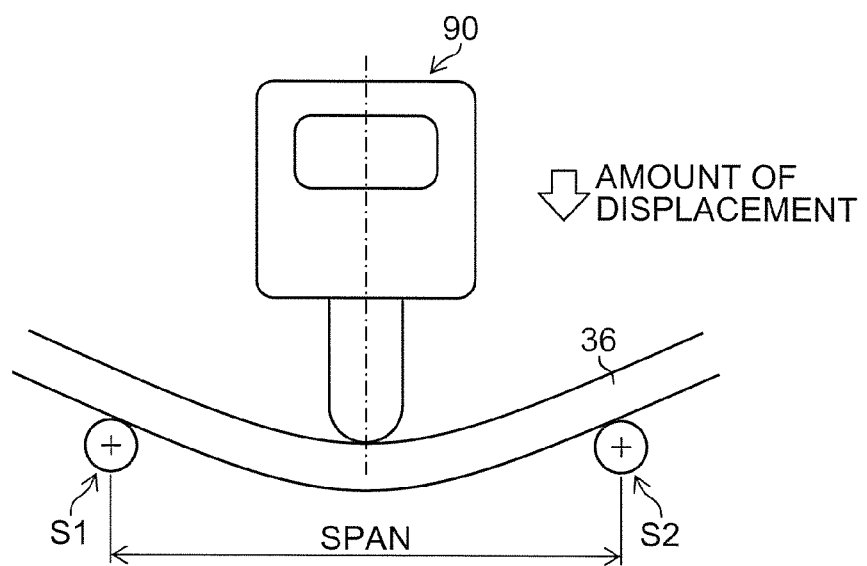

An example of a method of measuring the flexural rigidity in the flexible portion 36 will be described. As shown in FIGS. 5A and 5B, the flexural rigidity of the flexible portion 36 can be measured by the following steps of: supporting the flexible portion 36 at two points S1 and S2 in the longitudinal axial direction; applying a load to the midpoint between the two points to deform the flexible portion 36; and measuring a reaction force from the flexible portion 36, caused by the deformation of the flexible portion 36, with a force gauge 90. As an example of measurement conditions, a span (a distance between points S1 and S, which support the flexible portion 36, in the longitudinal axial direction) may be set to 30 mm to 200 mm, and a displacement (an amount of deformation of the flexible portion 36 in a direction orthogonal to the longitudinal axial direction (downward in FIGS. 5A and 5B) caused by the applied load) may be set to 5 mm to 50 mm. The measurement conditions of the flexural rigidity is not limited to the example above, and thus measurement conditions may be used properly depending on a length, the amount of displacement, and a level of flexural rigidity, of a portion to be measured.

(Configuration of Bending Portion)

The bending portion 38 has a configuration as follows: angle rings (not shown) that are rotatably connected to each other to constitute a structure; an outer periphery of the structure is coated with a net woven from metal wires; and the net is coated with an outer skin made of rubber. A plurality of operation wires (not shown) extend from the operation section 14 to the bending portion 38, and a distal end part of each of the operation wires is fixed to the angle ring of the distal end part constituting the bending portion 38. Accordingly, the bending portion 38 is bent up and down, and left and right, in response to operation of the angle knob 28 provided in the operation section 14. In addition, a balloon 39 is attached to an outer periphery of the bending portion 38 (refer to FIG. 1), and the balloon 39 is configured to be expanded or shrunk by fluid (such as air or water) supplied and discharged through a fluid conduit line (not shown) provided in the insertion section 12, as with the balloon 57 described above.

(Configuration of Distal End Hard Portion)

An optical system (such as lens, and an imaging element, which are not shown) for imaging the inside of a subject is built inside the distal end hard portion 40. In addition, a distal end face of the distal end hard portion 40 is provided with an observation window, an illumination window, an air/water supply nozzle, a forceps exit port, and the like, which are not shown. Behind the illumination window, there is provided an emission end of a light guide through which an illumination light from the light source device 24 is guided. The illumination light guided by the light guide is emitted toward a site to be observed inside the subject through the illumination window described above.

(Sliding Range of Insertion Section)

Figure 3:
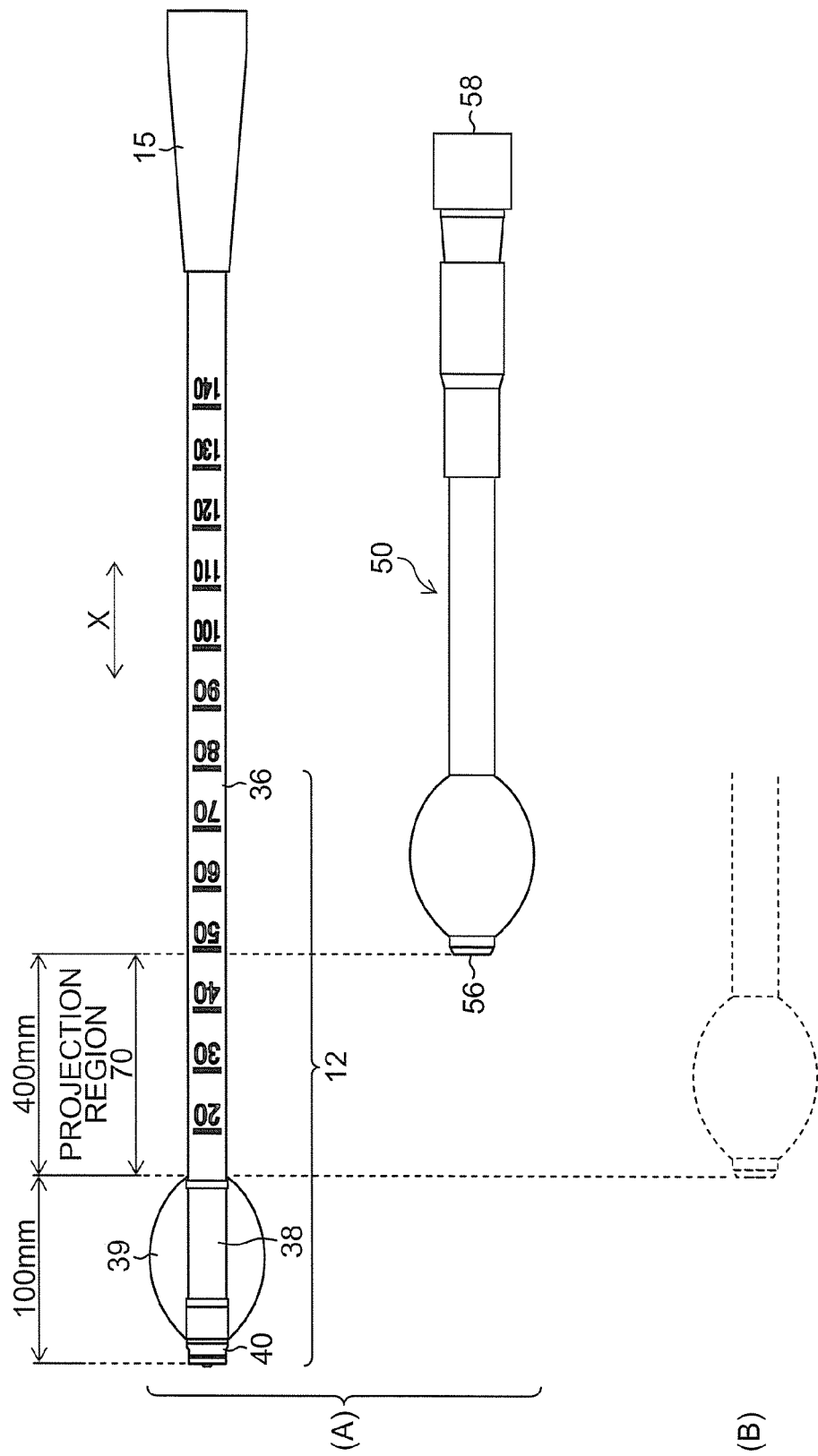
FIG. 3 shows a sliding range of an insertion section 12 with respect to an overtube 50.

Next, with reference to FIG. 3, a sliding range of the insertion section 12 with respect to the overtube 50 will be described. While the present embodiment describes a case where the effective length of the insertion section 12 is 1520 mm, and the overall length of the overtube 50 is 1050 mm, the present invention does not limit length of each of the insertion section 12 and the overtube 50 to this kind of case. FIG. 3 is prepared to clearly indicate a relationship between each element, and does not accurately reflect an actual size and shape.

Portion (A) in FIG. 3 shows a position relation between the insertion section 12 and the overtube 50, where the insertion section 12 is inserted into the overtube 50 and is slid (moved) until the boot 15 which is provided on a proximal end side of the insertion section 12 abuts on the overtube 50 (that is, until the insertion section 12 is positioned at a distal end position within a back-and forth movable range in which the insertion section 12 is movable with respect to the overtube 50). (Please note that, while FIG. 3 shows the insertion section 12 and the overtube 50 separately to clearly indicate the position relation, the insertion section 12 is actually inserted into the overtube 50.) In this position relation, an outer diameter of the boot 15 is equal to an inner diameter of the proximal end opening 58 of the overtube 50, and the overtube 50 abuts on the boot 15 to prevent the insertion section 12 from sliding further toward a distal end side of the overtube 50.

In a state shown in the Portion (A) in FIG. 3, the distal end hard portion 40, the bending portion 38, and a part of the flexible portion 36 (a part of a distal end side of the low flexural rigidity portion 36A) of the insertion section 12 project from the distal end opening 56 of the overtube 50 (refer to the Portion (A) in FIG. 3). In the present embodiment, the projecting part has a length of 500 mm, and hereinafter a region where a part of the flexible portion 36 projects, in the projecting part, is referred to as a "projection region 70". As described above, the balloon 39 is attached to the bending portion 38 and the bending portion 38 cannot slide in the overtube 50 (this state is shown in the Portion (B) in FIG. 3 by a dotted line). As a result, the flexible portion 36 can slide in the overtube 50 within a range of the projection region 70 (that is, a range between the states shown in the Portions (A) and (B) in FIG. 3).

In the present embodiment, it is assumed that the total length of the distal end hard portion 40 and the bending portion 38 is set to 100 mm. Thus, the length of the projection region 70 is 400 mm.

(Flexural Rigidity in Flexural Rigidity Varying Portion)

Next, a position and a range, where the flexural rigidity varying portion 36B is provided, as well as a value of flexural rigidity in the flexural rigidity varying portion 36B, will be described in detail. While the present embodiment describes the case where the insertion section 12 and the overtube 50 are inserted into around the stomach and the small intestine of the subject, a case where the endoscope system of the present invention is applicable is not limited to this kind of case.

FIG. 6 shows the flexural rigidity of the flexible portion 36 in the present embodiment. As shown in FIG. 6, in the present embodiment, a distal end position P0 in the projection region 70 is 100 mm away from the distal end of the insertion section 12, and the length of the projection region 70 is 400 mm (up to a position at 500 mm way from the distal end of the insertion section 12). In a region where the flexible portion 36 is covered with the overtube 50, which is beyond the most proximal end part in the projection region 70, the flexural rigidity is uniform (a minimum flexural rigidity portion) up to a first position P1 that is further 200 mm away from the most proximal end part toward the proximal end (up to a position 700 mm away from the distal end of the insertion section 12).

In the flexible portion 36, the minimum flexural rigidity portion from the distal end position P0 to the first position P1 is the low flexural rigidity portion 36A (first flexural rigidity uniform portion) described above. Then, a portion from the first position P1 to a second position P2 (900 mm away from the distal end of the insertion section 12) which is closer to the proximal end of the insertion section 12 than the first position P1 is the flexural rigidity varying portion 36B, and a portion toward the proximal end with respect to the second position P2 is the high flexural rigidity portion 36C (second flexural rigidity uniform portion). Thus, when the insertion section 12 is positioned at the distal end position within the back-and forth movable range with respect to the overtube 50 (the state shown in the Portion (A) in FIG. 3), that is, when the boot 15 provided on the proximal end side of the insertion section 12 abuts on the inner edge (contact part) of the proximal end opening 58 of the overtube 50, a part of the low flexural rigidity portion 36A projects from the distal end opening 56 of the overtube 50, and a proximal end position of the low flexural rigidity portion 36A (which is the same as the first position P1 on the distal end side of the flexural rigidity varying portion 36B) is located to be closer to a proximal end side of the overtube 50 than the distal end opening 56 in the longitudinal axial direction of the insertion section 12 (X direction in FIG. 3).

In this way, in an example shown in FIG. 6, the flexural rigidity in the low flexural rigidity portion 36A and the high flexural rigidity portion 36C is uniform in the longitudinal axial direction of the insertion section 12 (that is, an average rate of change of flexural rigidity is zero) and the flexural rigidity in the flexural rigidity varying portion 36B uniformly increases in the longitudinal axial direction of the insertion section 12. That is, an average rate of change of flexural rigidity in the flexural rigidity varying portion 36B is larger than the average rate of change of flexural rigidity in the low flexural rigidity portion 36A, and also larger than the average rate of change of flexural rigidity in the high flexural rigidity portion 36C. In the present embodiment, the "average rate of change of flexural rigidity" in the flexural rigidity varying portion 36B is a value expressed by $(Y-X)/Z$, when it is assumed that: X (at the distal end position P1) and Y (at the proximal end position P2) are values of the flexural rigidity in the flexural rigidity varying portion 36B; and Z is a length (length along the longitudinal axial direction of the insertion section 12) of the flexural rigidity varying portion 36C (here, X, Y, and Z are more than zero, and Y is more than X). Likewise, the average rate of change of the flexural rigidity of each of the low flexural rigidity portion 36A, and the high flexural rigidity portion 36C also can be defined.

Figure 7A:
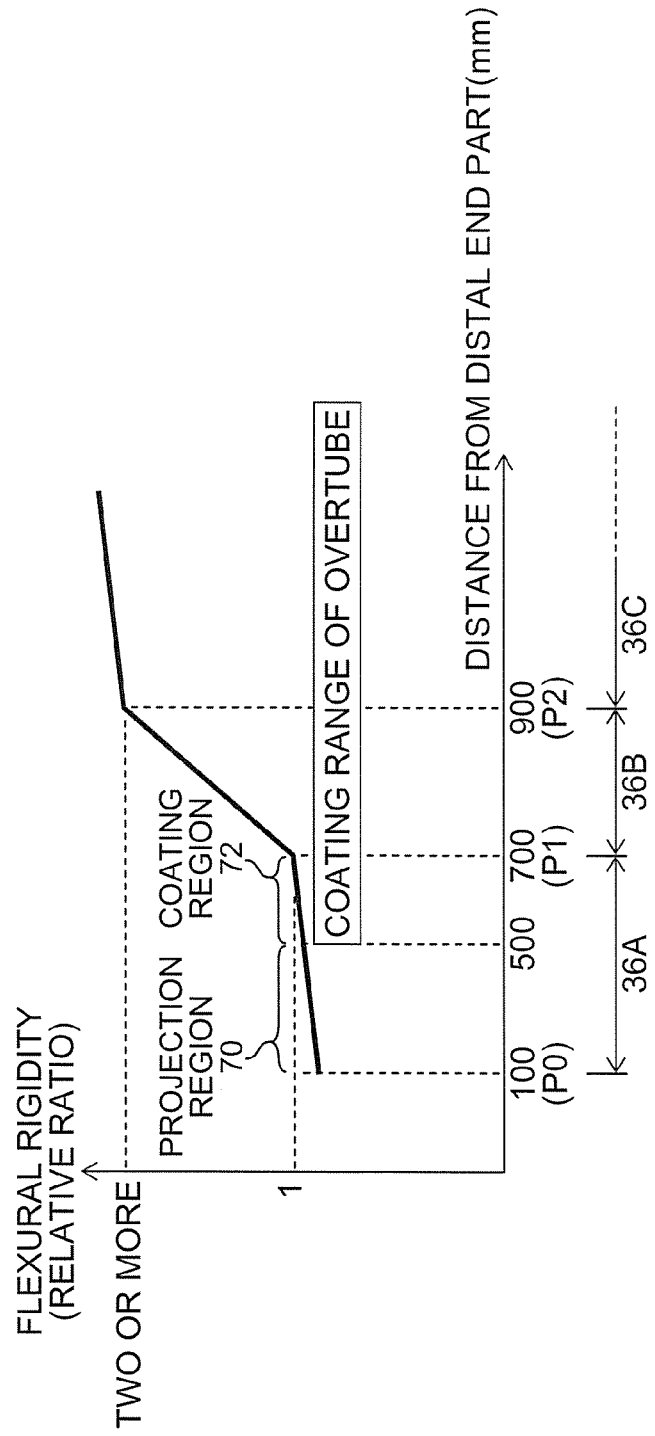
FIGS. 7A and 7B are more graphs showing examples of flexural rigidity of the flexible portion 36.
Figure 7B:
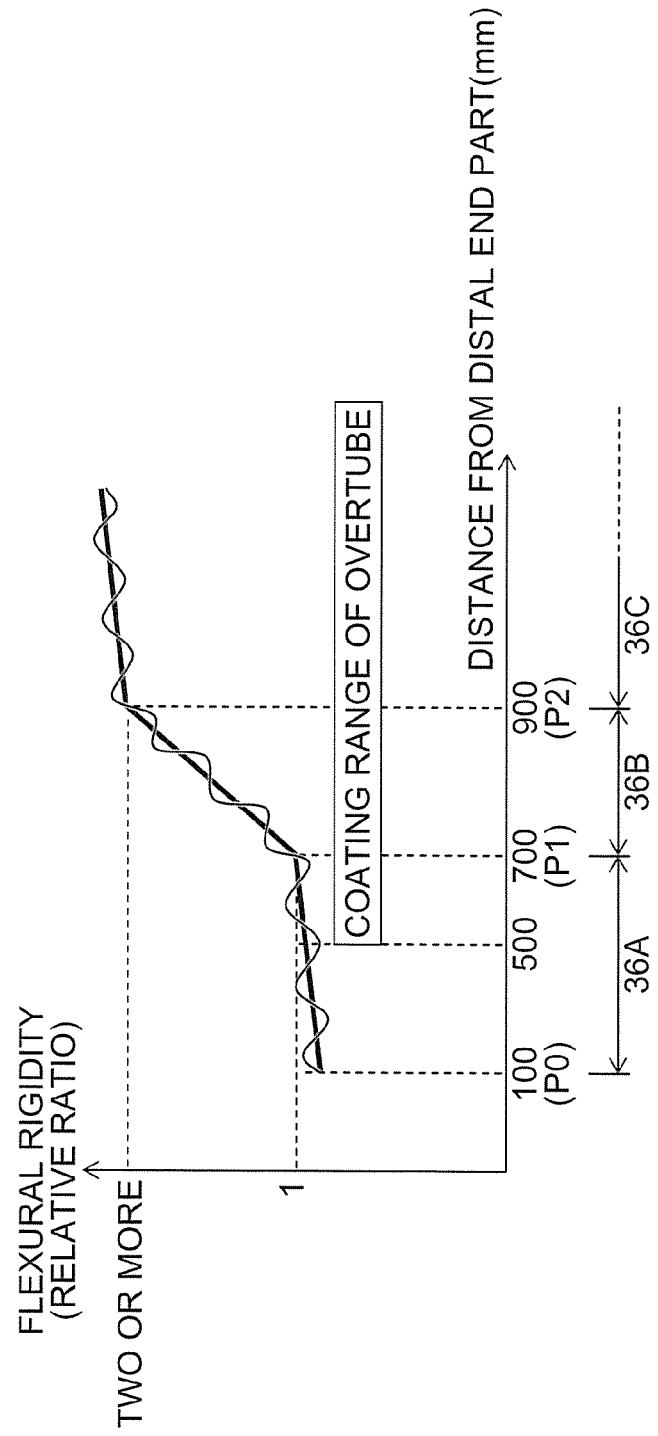

While FIG. 6 shows, as one of preferable aspects, the case where the flexural rigidity in the low flexural rigidity portion 36A and the high flexural rigidity portion 36C is uniform along a longitudinal direction of the flexible portion 36, the present invention is not limited to this kind of aspect. The flexural rigidity in each of the low flexural rigidity portion 36A and the high flexural rigidity portion 36C does not have to be always uniform. For example, even if the flexural rigidity in the low flexural rigidity portion 36A and the high flexural rigidity portion 36C varies within a variation range (an absolute value of difference between the flexural rigidity at the first position P1 on the distal end side and the flexural rigidity at the second position P2 on the proximal end side) smaller than the variation of flexural rigidity in the flexural rigidity varying portion 36B, the same effect as that shown in FIG. 6 can be achieved. FIG. 7A shows an example of varying the flexural rigidity in the low flexural rigidity portion 36A and the high flexural rigidity portion 36C, in this way. Here, while FIG. 7A shows an example of varying both of the flexural rigidity in the low flexural rigidity portion 36A and the flexural rigidity in the high flexural rigidity portion 36C, the flexural rigidity of any one of the low flexural rigidity portion 36A and the high flexural rigidity portion 36C may be varied. For example, the flexural rigidity in the low flexural rigidity portion 36A varies in the longitudinal axial direction of the insertion section 12. In addition, a rate of change of flexural rigidity in the low flexural rigidity portion 36A, the flexural rigidity varying portion 36B, and the high flexural rigidity portion 36C, does not have to be uniform in the longitudinal axial direction of the insertion section 12. As shown in FIG. 7B, the flexural rigidity may vary up and down (a curve in a graph of FIG. 7B) along an average rate of change of the flexural rigidity (a straight line in the graph of FIG. 7B). In this case, the flexural rigidity may periodically vary along the longitudinal axial direction of the insertion section 12, or may vary in a random manner.

Here, in FIG. 6, it is assumed that a coating region 72 (a range in which the flexible portion 36 is covered with the overtube 50) has a length of 200 mm, however, the length is an example of preferable values. Even if the length of the coating region 72 is varied within a range from 100 mm to 300 mm, the same effect as that of the example shown in FIG. 6 can be achieved. Likewise, in FIG. 6, it is assumed that the flexural rigidity varying portion 36B has a length of 200 mm, the length is an example of preferable values. Even if the length of the flexural rigidity varying portion 36B is varied within a range from 100 mm to 400 mm, the same effect as that of the example shown in FIG. 6 can be achieved.

In the present embodiment, the flexural rigidity in the flexural rigidity varying portion 36B uniformly increases from the distal end position (first position P1) toward the proximal end position (second position P2) (a rate of increase in the flexural rigidity is constant). The second flexural rigidity that is flexural rigidity at the second position P2 is more than twice the first flexural rigidity that is flexural rigidity at the first position P1. When the insertion section 12 and the overtube 50 are inserted into a subject, a small bent portion, and the like, may cause the distal end part of the insertion section 12 not to easily go forward depending on an insertion part to cause the flexible portion 36 to tend to be easily deformed in front (proximal end side) of the distal end part. However, in the present embodiment, the second flexural rigidity is set to be more than twice the first flexural rigidity to prevent the flexible portion 36 from being deformed on a proximal side, and the flexible portion 36 can be easily inserted.

(Insertion into Subject)

In the endoscope system 100 configured as above, the insertion section 12 and the overtube 50 can be inserted into a subject as below, for example. Specifically, firstly, an operator holds the holding section 52 and inserts the overtube 50 into a body from the mouth of the subject. When a predetermined length of the overtube 50 is inserted, the balloon control device 60 described above is controlled to expand the balloon 57 to fix the overtube 50 to the subject. In this state, the insertion section 12 is inserted into the insertion passage 59 of the overtube 50. Then, the insertion section 12 is inserted deep into the subject until the boot 15 abuts on an inner periphery of the proximal end opening 58. In this state, the insertion section 12 is positioned at the distal end position within the back-and-forth movable range in which the insertion section 12 is movable with respect to the overtube 50, and a part of the distal end side of the flexible portion 36 and the bending portion 38 are exposed from the distal end opening 56. Thus, the balloon control device 60 is controlled to expand the balloon 39 to fix the insertion section 12 to the subject. Subsequently, the balloon 57 is shrunk to release the fixing of the overtube 50 to the subject, and the overtube 50 is inserted deeper (until the distal end opening 56 is located at a proximal end part of the bending portion 38). Then, the balloon 57 is expanded to fix the overtube 50 to the subject, and the balloon 39 is shrunk to release the fixing of the insertion section 12 and the insertion section 12 is inserted deeper. Repeating that procedure enables the insertion section 12 and the overtube 50 to be inserted to a desired site of the subject. Here, when such the insertion operation is performed, the angle knob 28 is appropriately operated to bend the bending portion 38 up and down, left and right, to direct the distal end part of the insertion section 12 in a desired direction.

(Insertion Forward from Y-limb)

Figure 8:
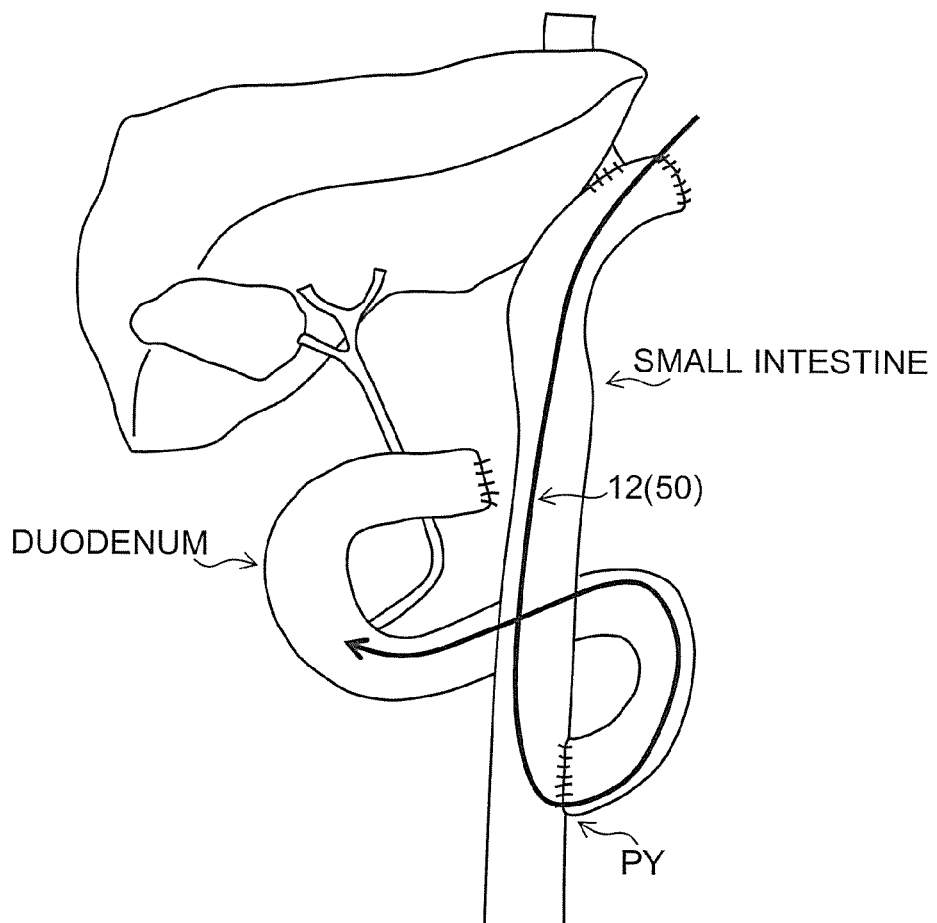
FIG. 8 shows a state where the insertion section 12 and the overtube 50 are inserted into a subject.

FIG. 8 shows a state when the insertion section 12 and the overtube 50 of the endoscope system 100 in accordance with the present embodiment are inserted into a subject from whom the stomach is completely removed. In the case of this kind of subject, a direction of the insertion section 12 needs to be greatly changed near a Y-limb (an anastomotic part between the small intestine and the duodenum) designated by reference character PY in FIG. 8. If the flexural rigidity of the insertion section is high, the insertion becomes difficult and the insertion causes a large load on the subject. In the endoscope system 100 in accordance with the present embodiment, the whole of a part to be inserted (maximum about 600 mm in length) beyond the Y-limb can be configured as the low flexural rigidity portion 36A (700 mm in length in the example above) that is a portion having a minimum flexural rigidity. As a result, the insertion into a duodenum with respect to the Y-limb can be facilitated, as well as a load on the subject, caused by the insertion, can be reduced.

(Relationship between Amount of Variation of Flexural Rigidity in Flexural Rigidity Varying Portion and Maximum Flexural Rigidity of Overtube)

Figure 9A:
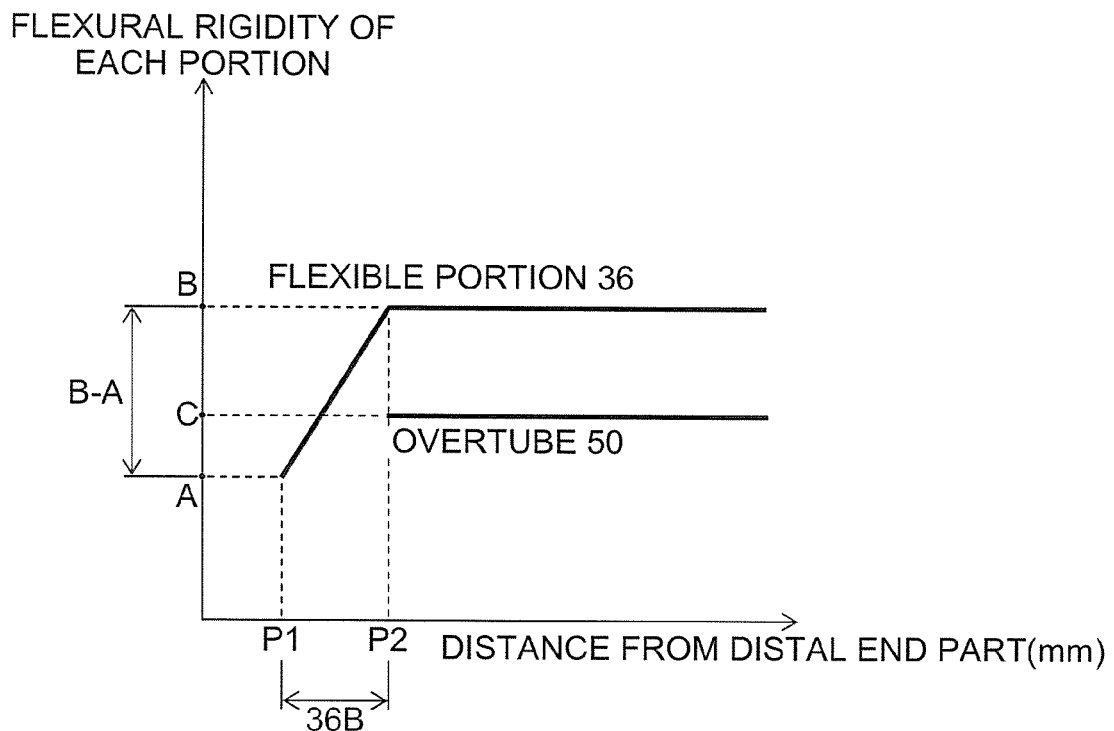
FIGS. 9A and 9B are graphs showing examples of relationship between flexural rigidity of the flexible portion 36 and flexural rigidity of the overtube 50.
Figure 9B:
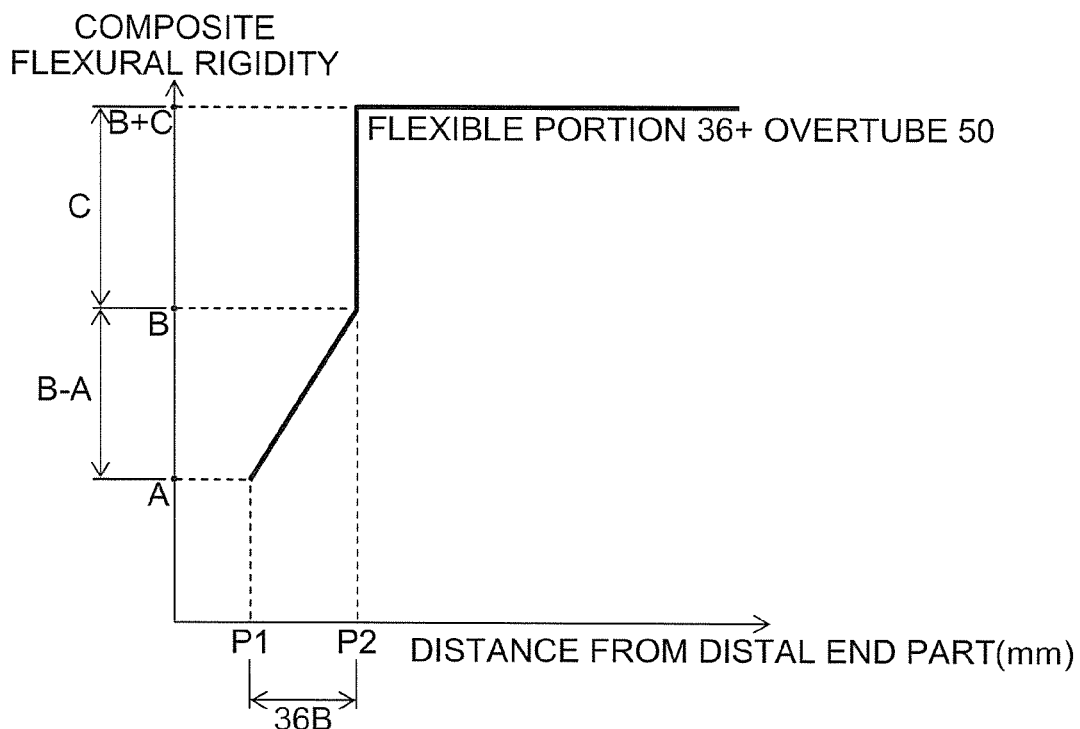

FIGS. 9A and 9B are graphs showing examples of a relationship between the amount of variation of flexural rigidity in the flexural rigidity varying portion and the maximum flexural rigidity of the overtube. If the variation of flexural rigidity in the flexural rigidity varying portion 36B is too small relative to the flexural rigidity of the overtube 50, the effect to be achieved by providing the flexural rigidity variation portion 36B decreases. Thus, in the present embodiment, a difference between the maximum flexural rigidity and the minimum flexural rigidity in the flexural rigidity varying portion 36B, is set to be more than a half of the maximum flexural rigidity of the overtube 50, as shown in FIGS. 9A and 9B.

Specifically, as shown in FIG. 9A, $(B-A)>\{(½)\times C\}$ is satisfied when it is assumed that: C is a value of the flexural rigidity of the overtube 50 alone (third flexural rigidity), and A (at the first position P1 that is the distal end position) and B (at the second position P2 that is the proximal end position) are values of the flexural rigidity in the flexural rigidity varying portion 36B (here, A, B, and C are more than zero, as well as B is more than A). In this case, a total sum of the flexural rigidity of the insertion section 12 and the flexural rigidity of the overtube 50 becomes as shown in FIG. 9B. Here, the example shown in FIGS. 9A and 9B describes the case where the flexural rigidity of the overtube 50 in the center axis direction is uniform. When the flexural rigidity of the overtube 50 varies along the center axis direction, the flexural rigidity at a position having the maximum flexural rigidity is assumed to be C and satisfy the relationship above.

As described above, the endoscope system 100 in accordance with the present embodiment can secure an appropriate flexural rigidity of the insertion section.

(Others)

In the embodiment above, when the insertion section 12 is positioned at the distal end position within the back-and-forth movable range in which the insertion section 12 is movable with respect to the overtube 50, the boot 15 abuts on the inner edge (contact part) of the proximal end opening 58 of the overtube 50 and performs positioning of the overtube 50 (identification and restriction of the proximal end position of the overtube 50). In contrast, positioning (identification and restriction of the distal end position of the overtube 50) when the insertion section 12 is positioned at the proximal end position within the back-and-forth movable range in which the insertion section 12 is movable with respect to the overtube 50, can be performed as shown in examples below, for example.

Example 1

Figure 10A:
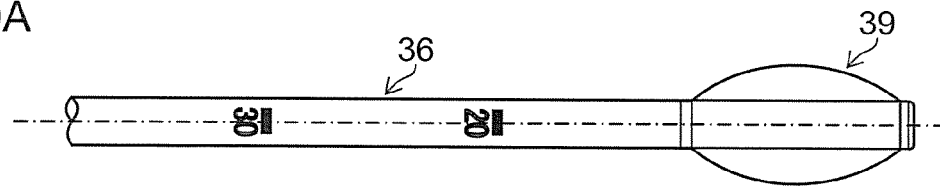
FIGS. 10A to 10G show examples of positioning when the insertion section 12 is positioned at a proximal end position within a back-and-forth movable range with respect to the overtube 50.

The positioning can be performed by allowing an inner edge of the distal end opening 56 of the overtube 50 and a proximal end side of the balloon 39 attached to the outer periphery of the bending portion 38 to be brought into contact with each other (refer to FIG. 10A). The positioning in the example 1 is applicable to so-called an endoscope of a double balloon type such as the aspect above, in which the balloons 39 and 57 are attached to the bending portion 38 and the overtube 50, respectively.

Example 2

Figure 10B:
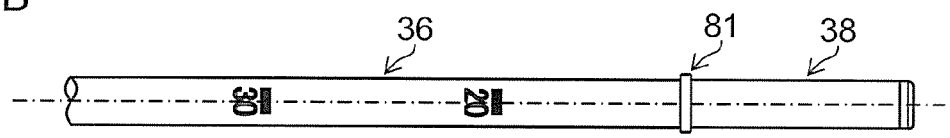

The positioning can be performed by allowing a fixing portion 81 provided on a proximal end side of the bending portion 38 and the inner edge of the distal end opening 56 of the overtube 50 to be brought into contact with each other (refer to FIG. 10B). The positioning in the example 2 is applicable not only to an endoscope of a double balloon type such as the aspect above, but also to an endoscope of a single balloon type, in which a balloon is attached to only a distal end of an insertion section.

Example 3

Figure 10C:
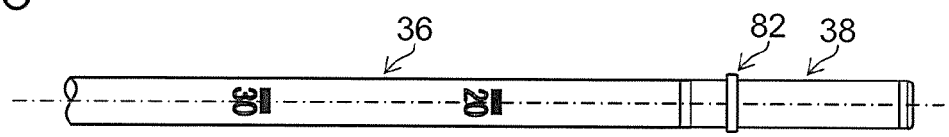

The positioning can be performed by providing a ring-shaped member 82 with an outer diameter larger than an outer diameter of the bending portion 38 in the middle of the bending portion 38 (middle of the insertion section 12 in the longitudinal axial direction) and allowing a distal end of the overtube 50 to abut on the ring-shaped member 82 (refer to FIG. 10C).

Example 4

Figure 10D:
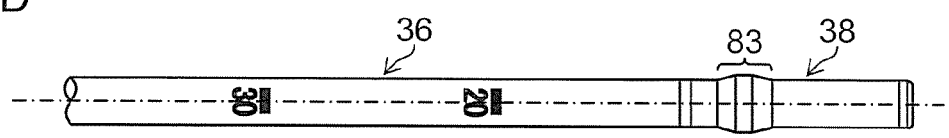

The positioning can be performed by providing a contact part 83 by partially thickening a part in the middle of the bending portion 38 (middle of the insertion section 12 in the longitudinal axial direction), and allowing the distal end of the overtube 50 to abut on the contact part 83 (refer to FIG. 10D).

Example 5

Figure 10E:
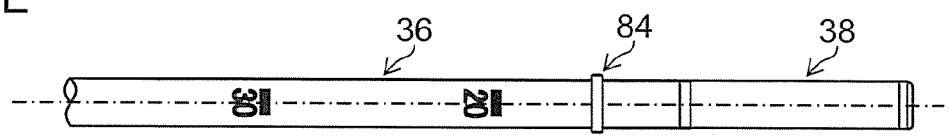

The positioning can be performed by providing a contact part 84 by fixing a member, such as a ring, to the distal end side of the flexible portion 36 with adhesive, and allowing the distal end of the overtube 50 to abut on the contact part 84 (refer to FIG. 10E).

Example 6

Figure 10F:
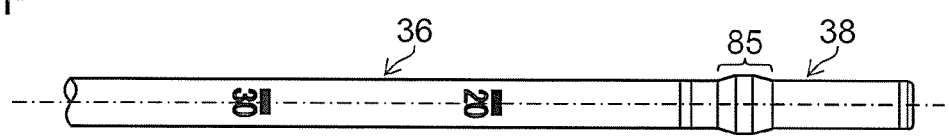
Figure 10G:
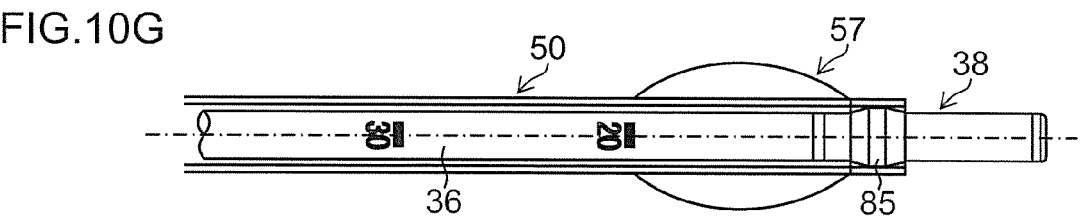

The positioning can be performed by providing an enlarged diameter part 85 by expanding a part in the middle of the bending portion 38 (middle of the insertion section 12 in the longitudinal axial direction) (refer to FIG. 10F), and fixing the enlarged diameter part 85 and an inner circumference of the overtube 50 to each other with a frictional force therebetween or a radial clamping force (refer to FIG. 10G).

The present invention is not limited to the embodiments described above, and a variety of modifications are possible within a range without departing from the spirit of the present invention.

What is claimed is:

1. An endoscope system comprising:
   an endoscope including: an insertion section to be inserted into a body; and an operation section connected to a proximal end side of the insertion section, the insertion section having a distal end hard portion, a bending portion connected to a proximal end side of the distal end hard portion and a flexible portion connected to a proximal end side of the bending portion; and
   an insertion auxiliary tool including a tube body having a distal end opening, a proximal end opening and an insertion passage into which the insertion section is inserted from the proximal end opening, the insertion section being movable back and forth along a center axis direction of the tube body, the tube body being configured to have a length that allows at least a part of the flexible portion to project from the distal end opening when the insertion section is positioned at a distal end position within a back-and-forth movable range in which the insertion section is movable with respect to the tube body, wherein
   the flexible portion includes:
   a low flexural rigidity portion that is positioned on a distal end side of the flexible portion; and
   a flexural rigidity varying portion connected to a proximal end side of the low flexural rigidity portion, the flexural rigidity varying portion having a flexural rigidity which increases from a low flexural rigidity portion side toward a proximal end side of the flexural rigidity varying portion, wherein
   the flexural rigidity varying portion has an average rate of change of flexural rigidity in a longitudinal axial direction of the insertion section, the average rate of change of flexural rigidity being larger than an average rate of change of flexural rigidity in the low flexural rigidity portion in the longitudinal axial direction of the insertion section,
   when a flexural rigidity at a distal end position of the flexural rigidity varying portion is indicated as a first flexural rigidity, a flexural rigidity at a proximal end position of the flexural rigidity varying portion is indicated as a second flexural rigidity, and a flexural rigidity of the tube body at a position of the tube body having a maximum flexural rigidity is indicated as a third flexural rigidity, a difference between the first flexural rigidity and the second flexural rigidity is more than a half of the third flexural rigidity.

2. The endoscope system according to claim 1, wherein, the second flexural rigidity is more than twice the first flexural rigidity.

3. The endoscope system according to claim 1, wherein, the low flexural rigidity portion includes a first flexural rigidity uniform portion in which a flexural rigidity is uniform along the longitudinal axial direction of the insertion section.

4. The endoscope system according to claim 1, wherein, the flexural rigidity in the flexural rigidity varying portion uniformly increases from the low flexural rigidity portion side toward the proximal end side of the flexural rigidity varying portion.

5. The endoscope system according to claim 1, wherein, the flexural rigidity varying portion includes a first resin layer and a second resin layer having a flexural rigidity larger than that of the first resin layer, and the first resin layer is reduced in thickness from the distal end position of the flexural rigidity varying portion toward the proximal end position of the flexural rigidity varying portion.

6. The endoscope system according to claim 1, wherein, the flexural rigidity varying portion includes a first resin and a second resin having a flexural rigidity larger than that of the first resin, and a ratio of the second resin is increased from the distal end position of the flexural rigidity varying portion toward the proximal end position of the flexural rigidity varying portion.

7. The endoscope system according to claim 1, wherein, the endoscope is configured to be inserted into a stomach and a small intestine.

8. The endoscope system according to claim 1, wherein, the endoscope is configured to be inserted into an anastomotic part between a small intestine and a duodenum.

9. The endoscope system according to claim 1, further comprising a balloon attached to a distal end part of the tube body.

10. The endoscope system according to claim 1, wherein, when the insertion section is positioned at the distal end position within the back-and-forth movable range in which the insertion section is movable with respect to the tube body, a position of the proximal end of the low flexural rigidity portion is positioned between the distal end opening of the tube body and the proximal end opening of the tube body in the longitudinal axial direction of the insertion section.

11. The endoscope system according to claim 1, wherein, the flexible portion includes a high flexural rigidity portion that is positioned on a proximal end side of the flexible portion, the high flexural rigidity portion having increased flexural rigidity relative to the low flexural rigidity portion.

12. The endoscope system according to claim 1, further comprising a balloon attached to a distal end part of the tube body,
wherein the endoscope is configured to be inserted into a stomach and a small intestine.

13. The endoscope system according to claim 5, further comprising a balloon attached to a distal end part of the tube body,
wherein the endoscope is configured to be inserted into a stomach and a small intestine.

14. The endoscope system according to claim 6, further comprising a balloon attached to a distal end part of the tube body,
wherein the endoscope is configured to be inserted into a stomach and a small intestine.

15. The endoscope system according to claim 1, further comprising a balloon attached to a distal end part of the tube body,
wherein the endoscope is configured to be inserted into a stomach and a small intestine, and
when the insertion section is positioned at the distal end position within the back-and-forth movable range in which the insertion section is movable with respect to the tube body, a position of the proximal end of the low flexural rigidity portion is positioned between the distal end opening of the tube body and the proximal end opening of the tube body in the longitudinal axial direction of the insertion section.

16. The endoscope system according to claim 5, further comprising a balloon attached to a distal end part of the tube body,
wherein the endoscope is configured to be inserted into a stomach and a small intestine, and
when the insertion section is positioned at the distal end position within the back-and-forth movable range in which the insertion section is movable with respect to the tube body, a position of the proximal end of the low flexural rigidity portion is positioned between the distal end opening of the tube body and the proximal end opening of the tube body in the longitudinal axial direction of the insertion section.

17. The endoscope system according to claim 6, further comprising a balloon attached to a distal end part of the tube body,
wherein the endoscope is configured to be inserted into a stomach and a small intestine, and
when the insertion section is positioned at the distal end position within the back-and-forth movable range in which the insertion section is movable with respect to the tube body, a position of the proximal end of the low flexural rigidity portion is positioned between the distal end opening of the tube body and the proximal end opening of the tube body in the longitudinal axial direction of the insertion section.

* * * * *